(12) United States Patent
Fantigrossi et al.

(10) Patent No.: US 10,729,482 B2
(45) Date of Patent: Aug. 4, 2020

(54) BONE FIXATION DEVICE

(71) Applicant: MEDACTA INTERNATIONAL SA, Castel San Pietro (CH)

(72) Inventors: Alfonso Fantigrossi, Turate (IT); Meinrad Fiechter, Lugano (CH); Andrea Tettamanzi, Cantu' (IT); Francesco Siccardi, Castel San Pietro (CH); Clément Max Leonard Werner, Männedorf (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 309 days.

(21) Appl. No.: 15/557,877

(22) PCT Filed: Mar. 9, 2016

(86) PCT No.: PCT/IB2016/051321
§ 371 (c)(1),
(2) Date: Sep. 13, 2017

(87) PCT Pub. No.: WO2016/147080
PCT Pub. Date: Sep. 22, 2016

(65) Prior Publication Data
US 2018/0049789 A1 Feb. 22, 2018

(30) Foreign Application Priority Data

Mar. 13, 2015 (IT) .............................. MI2015A0385

(51) Int. Cl.
*A61B 17/86* (2006.01)
*A61B 17/88* (2006.01)
*A61B 17/68* (2006.01)

(52) U.S. Cl.
CPC ........ *A61B 17/8605* (2013.01); *A61B 17/685* (2013.01); *A61B 17/8695* (2013.01); *A61B 17/88* (2013.01)

(58) Field of Classification Search
CPC .......................... A61B 17/685; A61B 17/8695
See application file for complete search history.

(56) References Cited

U.S. PATENT DOCUMENTS

| 4,408,601 | A | * | 10/1983 | Wenk | ................ | A61B 17/8014 |
| | | | | | | 606/282 |
| 7,967,848 | B2 | * | 6/2011 | Abdelgany | ........ | A61B 17/7037 |
| | | | | | | 606/266 |

(Continued)

FOREIGN PATENT DOCUMENTS

EP 1813216 A1 8/2007

OTHER PUBLICATIONS

International Search Report and Written Opinion dated Jun. 16, 2016 from International Application No. PCT/IB2016/051321, 10 pages.

*Primary Examiner* — Nicholas W Woodall
(74) *Attorney, Agent, or Firm* — Meunier Carlin & Curfman LLC

(57) ABSTRACT

A bone fixation device (1) comprises an elongated member (2) and a washer (3) assembled in a manner to prevent relative longitudinal displacement at the same time allowing axial rotation of the washer (3) with respect of the elongated member (2). The elongated member (2) comprises a proximal head (4) and an elongated shaft (5). The proximal head (4) comprises at least a distal spherical portion (8) having a diameter (D) and defining a maximum transversal dimension (Dh) of the proximal head (4). The washer (3) has a central cavity (14) configured to seat the proximal head (4) and comprising a central spherical portion (15) having the same diameter (D) of the distal spherical portion (8) of the proximal head (4). The central spherical portion (15) extends between a distal rim (16) and a proximal rim (17). The distal rim (16) has a distal transversal dimension (Dd) larger than a maximum transversal dimension (d) of the elongated shaft (Continued)

(5) and smaller than the maximum transversal dimension (Dh) of the proximal head (4). The proximal rim (17) has a proximal transversal dimension (Dw) larger than the maximum transversal dimension (d) of the elongated shaft (5) and slightly smaller than the maximum transversal dimension (Dw) of the proximal head (4). The proximal transversal dimension (Dw) of the proximal rim (17) is larger than the distal transversal dimension (Dd) of the distal rim (16). The proximal rim (17) is configured to be elastically deformable by pressing the proximal head (4) through the proximal rim (17).

13 Claims, 6 Drawing Sheets

(56) References Cited

U.S. PATENT DOCUMENTS

| | | | |
|---|---|---|---|
| 8,585,743 B2* | 11/2013 | Ampuero | A61B 17/8605 606/290 |
| 8,641,733 B2* | 2/2014 | Chin | A61B 17/1757 606/246 |
| 9,044,277 B2* | 6/2015 | O'Neil | A61B 17/7064 |
| 10,335,216 B2* | 7/2019 | Mari | A61B 17/863 |
| 2009/0192551 A1* | 7/2009 | Cianfrani | A61B 17/686 606/301 |
| 2016/0095639 A1* | 4/2016 | Elsbury | A61B 17/8695 606/308 |

\* cited by examiner

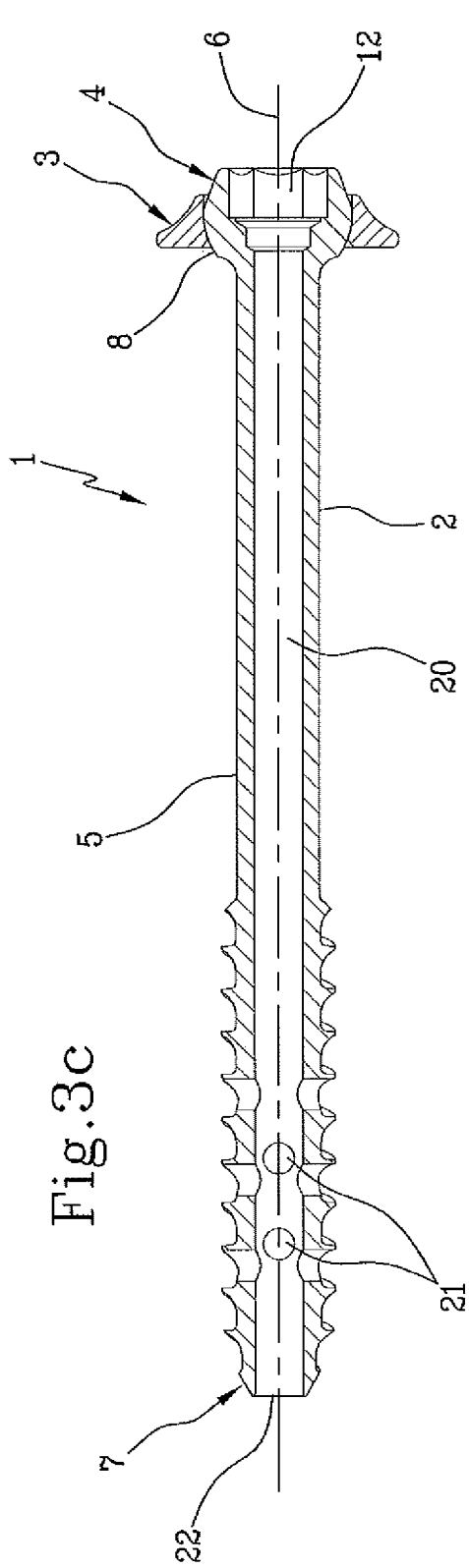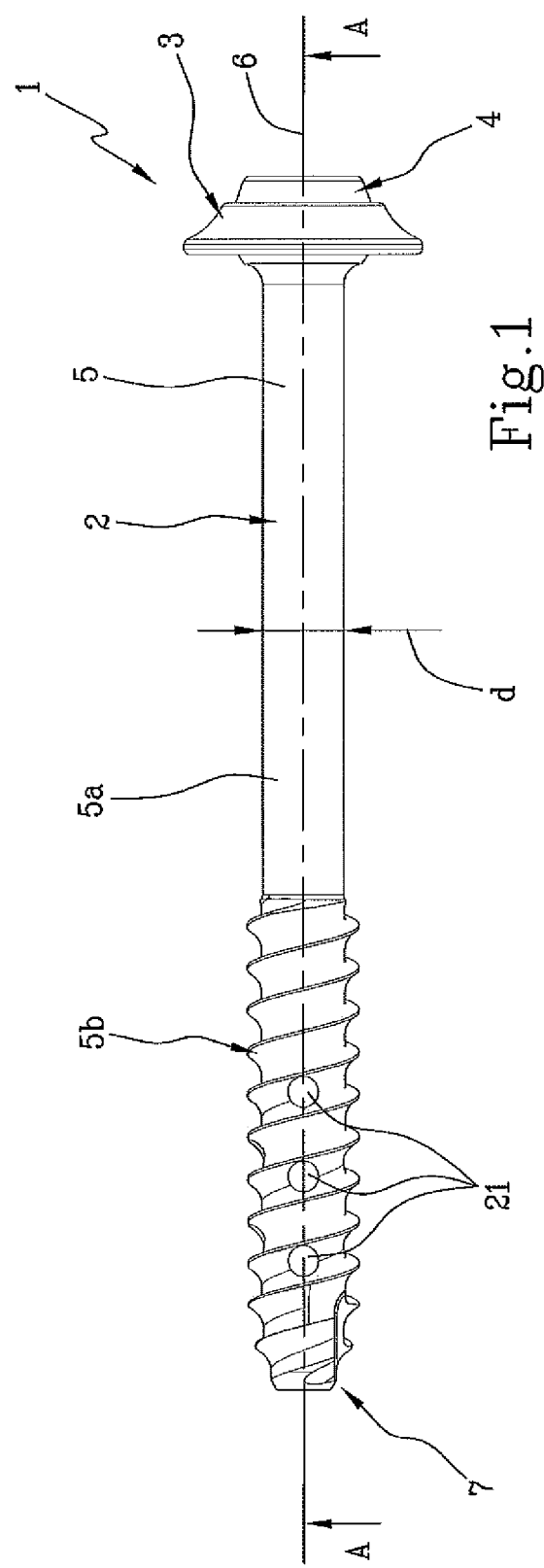

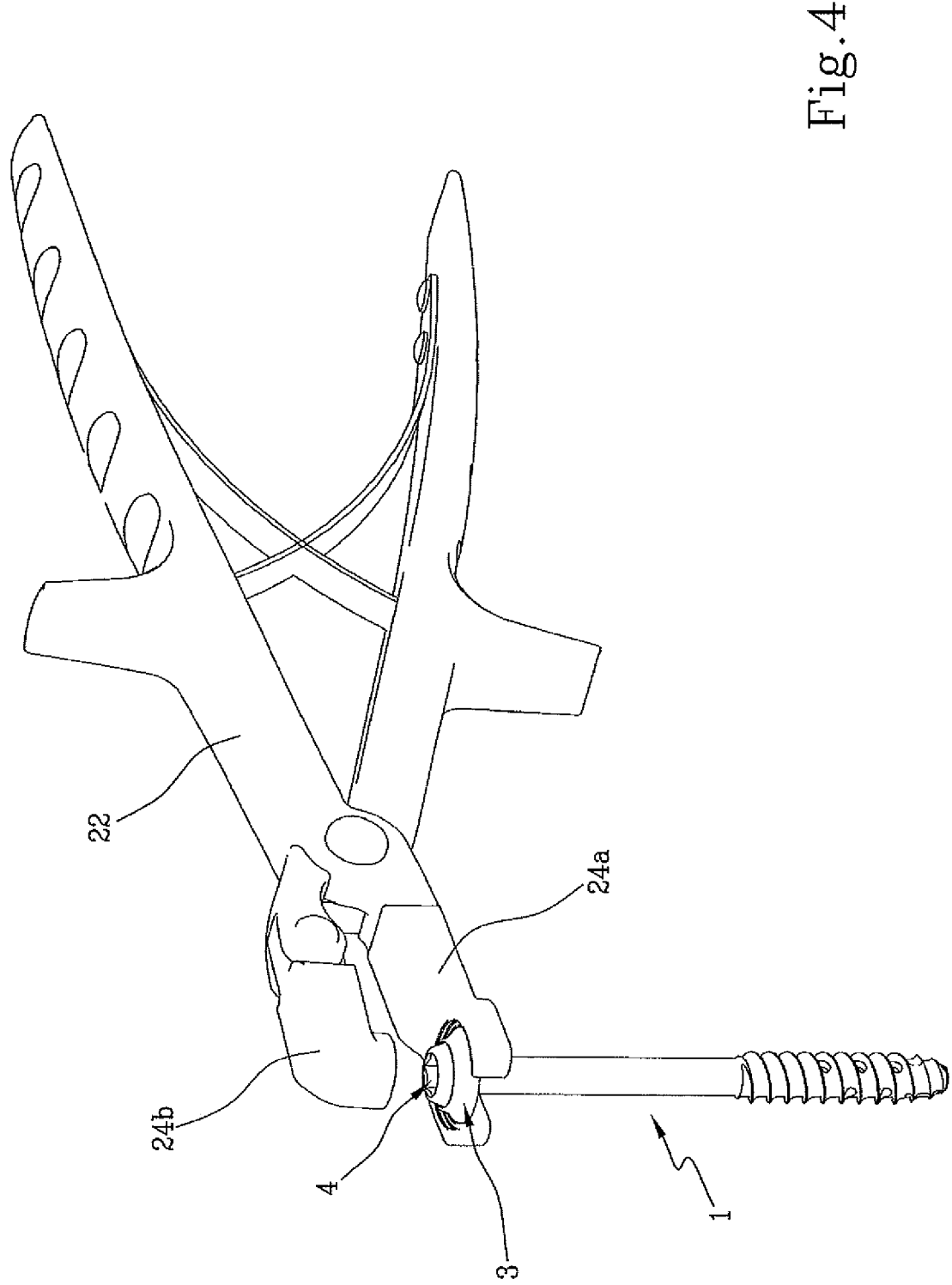

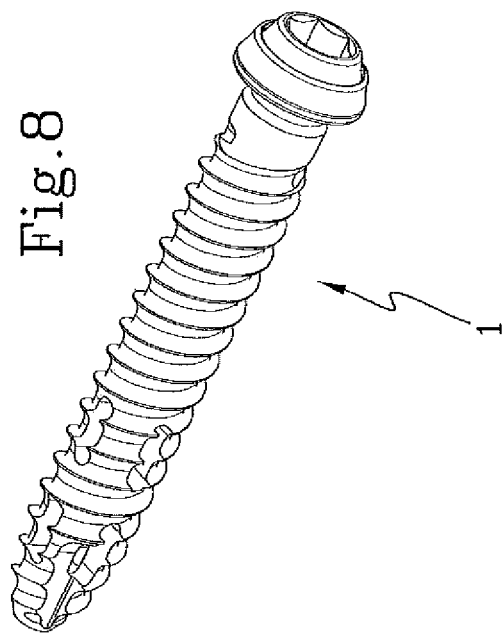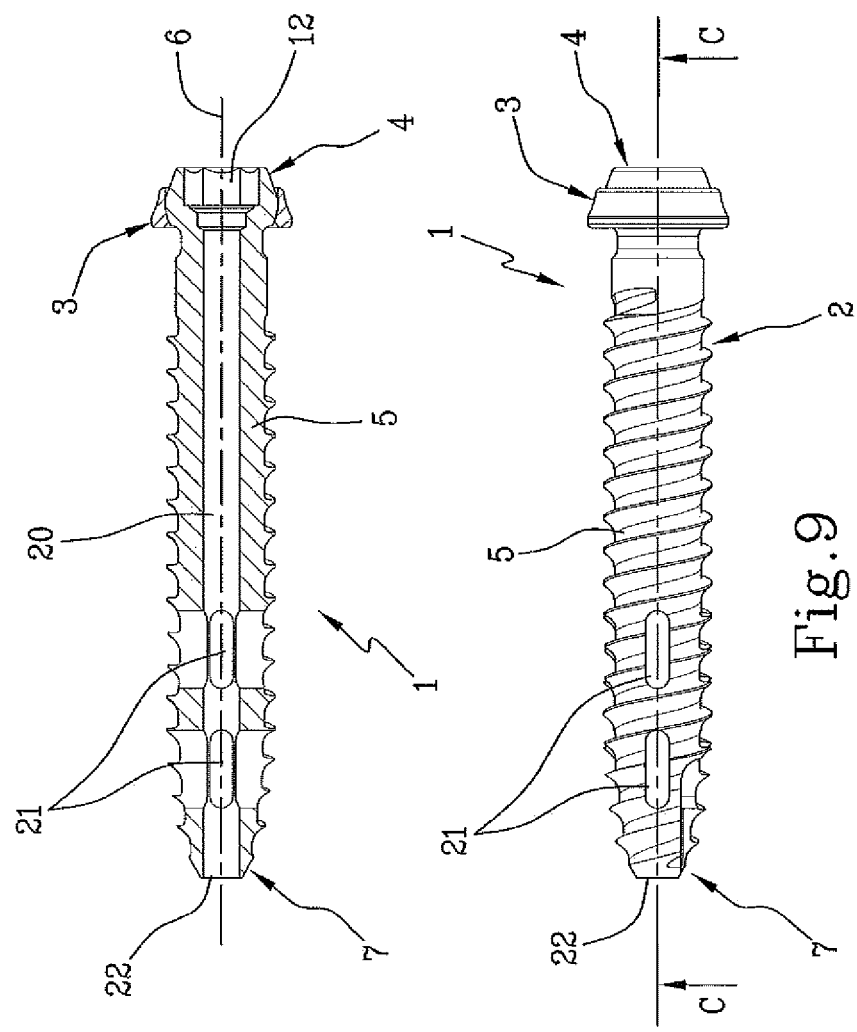

BONE FIXATION DEVICE

The present invention relates to a bone fixation device and a bone fixation kit comprising the bone fixation device.

The present invention relates to both trauma applications, in particular for the fixation of fractures of long bones or pelvic bone, and artrodesis applications, in particular SI-Joint artrodesis that is the fixation of the Sacro-Iliac joint for stabilization and fusion of the same usually applied in case of joint disruption or degenerative sacroiliitis.

In trauma applications, bone fractures are typically treated by restoring the fractured pieces of bone to their natural positions, and maintaining those positions while the bone heals. Accurate alignment and fixation of the broken bone parts is important for improving long-term functional results of such injuries. For uncomplicated fractures, casts or other external fixation means are commonly used to stabilize the bone. However, in particular when it comes to fixation of complicated fractures, such as rotationally unstable joint injuries, internal fixation by means of screws and bone plates have proven effective.

Such internal fixation devices allow for fixating the fractured joint or bone parts in their correct position and thereby promote healing of the fracture. However in case of complex fractures or complex joints, like the sacro-iliac (SI) articulation, diagnosis and fixation can be difficult, in particular when applying newer techniques of minimal invasive procedures, e.g. closed or limited open reduction, coupled with percutaneous stabilization.

Although numerous different approaches for internal bone fixation have been developed, choices of suitable screws and surgical tools are still very limited.

One complication associated with internal bone fixation, and in particular joint fixation, is migration of the screw over time owing to normal physiologic movement and remodelling of the bone. Depending on the bone density and structure, the screws either tend to migrate out of the bone, leading to loosening of the screw, or to migrate into the bone, which significantly complicates removal of the screws after the fracture has healed or the joint has been stabilized.

The risk of migration of bone screws into the bone can be reduced by the use of washers which provide an increased retention surface and can further provide a compressive force on the bone region. Indeed trauma screws and sacro-Iliac (SI) screws are often used in combination with washers to improve retention surface and prevent screw migration into the bone. The washer is usually not stably coupled to the screw, but only affixed below the screw head and acting as a mechanical stop, allowing the screw to rotate and angulate independently from the washer.

However, the benefits provided by the washer are partly offset by the difficulty to remove the washer together with the screw later-on after the injury has healed. In the worst case, the washer forms a strong attachment to the bone, whereas the screw loosens and migrates out of the bore. This not only impairs the fixation of the fracture or of the joint but also complicates removal of both, the migrated screw and the attached washer from the body.

Moreover known trauma screws and sacro-Iliac (SI) screws are usually provided with a pre-assembled washer, whereby the surgeon can only choose between screws pre-assembled with a corresponding washer or screws without washer.

In addition loosening and migration of bone screws is exacerbated inter alia by inadequate primary position of the screw. For example, ideal positioning of a screw in the pelvic region is particularly difficult due to the complex anatomy and hard-to-access areas of the pelvis, especially of the posterior pelvic ring.

It is therefore an object of the present invention to provide a bone fixation device for accurate stabilization of an articulated joint, in particular a SI-Joint, or a bone fracture, in particular of pelvic ring fractures, that provides increased screw migration resistance and at the same time allows for secure removal of all components of the bone fastening system after the healing process is complete.

It is therefore a further object of the present invention to provide a bone fixation device which can be easily assembled intraoperative, during the surgery.

This problem is solved by the bone fastening system according to claim 1. Dependent claims correspond to further embodiments of the invention.

The bone fixation device comprises an elongated member and a washer suitable to be assembled in a manner to prevent relative longitudinal displacement at the same time allowing axial rotation of the washer with respect of the elongated member. The elongated member comprises a proximal head and an elongated shaft extending from the proximal head along a shaft axis towards a distal end of the elongated member. The proximal head comprises at least a distal spherical portion having a diameter and defining a maximum transversal dimension of the proximal head with respect to the shaft axis.

The washer has a central cavity configured to seat the proximal head and comprising a central spherical portion having the same diameter of the distal spherical portion of the proximal head. The central spherical portion extends along a washer axis between a distal rim and a proximal rim.

The distal rim has a distal transversal dimension larger than a maximum transversal dimension of the elongated shaft and smaller than the maximum transversal dimension of the proximal head, with respect to the washer axis and the shaft axis.

The proximal rim has a proximal transversal dimension larger than the maximum transversal dimension of the elongated shaft and slightly smaller than the maximum transversal dimension of the proximal head, with respect to the washer axis and the shaft axis.

The proximal transversal dimension of the proximal rim is larger than the distal transversal dimension of the distal rim. The proximal rim is configured to be elastically deformable by pressing the proximal head through the proximal rim along the shaft axis and washer axis.

Thanks to the interference between the proximal rim and spherical portion of the proximal head the elongated member and the can be handled as one unit and can easily be removed after fracture healing without risking that one component remains attached to the bone after removal.

In line with the present invention, the washer defines a central cavity for accommodating the proximal head of the elongated member whereby the proximal head is at least partly surrounded by the central cavity. Nevertheless, the proximal head can freely rotate around the washer axis. This has the effect that the washer does not apply additional rotational resistance to the elongated member and avoids that an increased amount of torque needs to be applied during fastening. At the same time, the risk of migration decreases.

In general, the elongated member is a cannulated screw having an elongated screw shaft which can be of constant diameter or of variable diameter, e.g. with conically shaped shaft widening from the tip towards the proximal head. In a preferred embodiment the elongated member comprises an axial channel extending along the shaft axis through the proximal head and the elongated shaft and opening out into the exterior through a primary fenestration arranged at the distal end of the elongated shaft. This allows for the injection of bone cement around the screw threads in order to increase the strength of fixation of the screw in the bone and to fill the fracture void. In addition, cement formulations with antibiotics or osteoinductive proteins can be introduced if there are indications of inflammation or osteoporosis.

The outer thread may be of a self-tapping kind that does not require a thread being pre-cut into the bone.

The outer diameter of the washer may vary depending upon the needs and desires of the particular bone structure. Thus, the washer may have a disc shape of various sizes or irregular shape.

The length of the elongated shaft is preferably up to 180 mm for trauma application or shorter for SI-Joint Arthrodesis.

The components of the bone fixation device can be prepared from any biologically acceptable materials suitable for medical applications, including metals and ceramics. It goes without saying that the components can be made from different materials or all from the same material. Examples of preferred materials are commercially pure titanium, titanium alloys, cobalt-chrome alloys, stainless steel alloys, super-elastic metallic alloys and ceramic materials. The components of the bone fixation device also be fabricated from a combination of two or more of the above-described materials.

In a preferred embodiment, the components of the bone fixation device consist of titanium, a titanium alloy or stainless steel. These materials are particularly well suited, since they demonstrate sufficient stability for application in the field of bone fastening and can also be brought into the desired shape without difficulty. In addition, components made of these materials can be easily cleaned and sterilized, which is vital for application in surgical procedures in order to prevent infections and other undesirable side effects.

The bone fixation device of the present invention is preferably employed in the treatment of a pelvic pathology and more preferably in the treatment of a degenerative disease of the iliosacral joint requiring stabilization and/or the fracture management of the pelvic ring, in particular high energy fracture of the pelvic ring, iliosacral joint disruption and associated pelvic fracture, osteoporotic fracture of the sacrum and/or acetabulum fracture. Nevertheless, it is contemplated that the bone fixation device of the present invention can be employed with other applications for the treatment of fractured bones.

In a preferred embodiment, the distal rim is disposed at a side of the washer facing the elongated shaft when assembled with the washer.

In a preferred embodiment, the maximum transversal dimension of the proximal head is smaller than the diameter of the spherical portion of the proximal head.

In a preferred embodiment, the central cavity of the washer comprises a conical diverging portion outwardly extending from said distal rim along the washer axis towards said elongated shaft, when assembled with the washer.

In a preferred embodiment, the central cavity of the washer comprises a cylindrical portion outwardly extending from said proximal rim along the washer axis.

In a preferred embodiment, the proximal head comprises a proximal conical portion extending proximally along the shaft axis. The proximal conical portion has a maximum transversal dimension defined by the maximum transversal dimension of the proximal head and a minimum transversal dimension defining a proximal surface of the proximal head, with respect to the shaft axis.

In a preferred embodiment, the proximal conical portion comprises at the proximal surface a tool receiving seat suitable for receiving an insertion tool.

In a preferred embodiment, the proximal head comprises a central cylindrical portion extending proximally from the distal spherical portion along the shaft axis at the maximum transversal dimension of the proximal head.

In a preferred embodiment, the proximal conical portion extends proximally from the central cylindrical portion along the shaft axis.

In a further aspect, the present invention provides a kit comprising at least one bone fixation device described above and an assembling device configured to overcome the interference between the proximal head and the proximal rim and to push the proximal head into the central cavity of the washer.

The assembling device comprises a seat suitable for receiving the washer.

The number of individual components within this kit can of course be varied as desired.

The present invention is further illustrated by way of the attached figures which are described in detail in the following section and of which FIG. 1 shows a side view of an embodiment of a bone fixation device according to the present invention;

FIG. 3b shows a cross section view of the detail of FIG. 3a

FIG. 3c shows a cross section view A-A of the bone fixation device of FIG. 1;

FIG. 4 shows a perspective view of the bone fixation kit according to the present invention;

FIG. 8 shows a perspective view of an embodiment of a bone fixation device according to the present invention;

FIG. 9 shows a side view of the bone fixation device of FIG. 8;

FIG. 10 shows a cross section view C-C of the bone fixation device of FIG. 9.

A bone fixation device 1 has been shown in FIG. 1 and comprises an elongated member 2 and a washer 3 assembled in a manner to prevent relative longitudinal displacement at the same time allowing axial rotation of the washer 3 with respect of the elongated member 2.

Figure 3A:
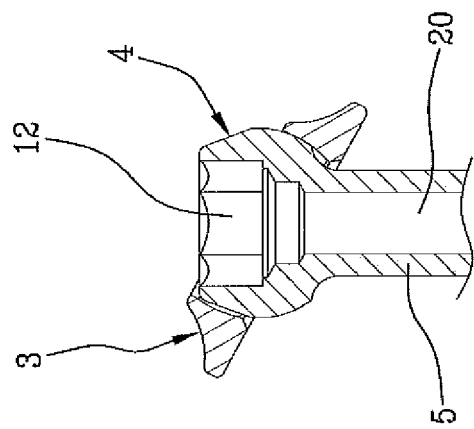
FIG. 3a shows an enlarged detail of FIG. 1 in a possible configuration.
Figure 3B:
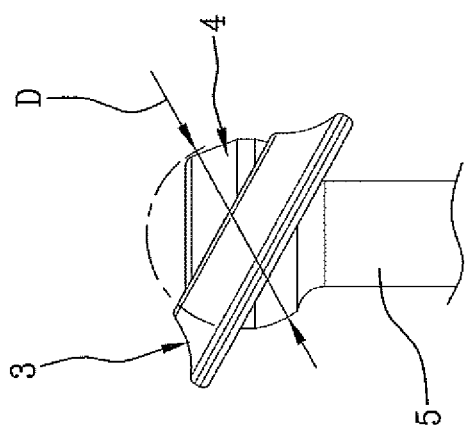
Figure 2:
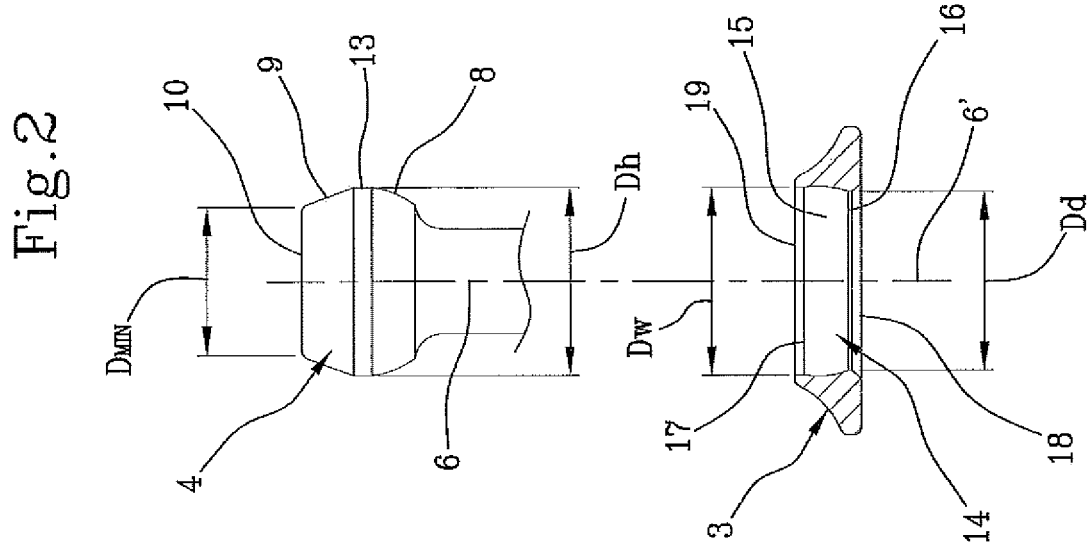
FIG. 2 shows a cross-section partial view of the bone fixation device of FIG. 1 in an assembling configuration.

Embodiment of FIGS. 1 and 3c is related in particular to trauma applications. The elongated member 2 is longer than 100 mm.

With reference to the following description, the term "proximal" has been used with reference to those parts/components near the surgeons and the tool used for implanting the bone fixation device and the term "distal" has been used with reference to those parts/components far from the surgeons and the tool used for implanting the bone fixation device.

The elongated member 2 comprises a proximal head 4 and an elongated shaft 5 extending from the proximal head along a shaft axis 6 towards a distal end 7 of the elongated member 2.

The proximal head 4 comprises at least a distal spherical portion 8 having a diameter D and defining a maximum transversal dimension Dh of the proximal head 4 with respect to the shaft axis 6.

In particular the maximum transversal dimension Dh of the proximal head 4 is smaller than the diameter D of the spherical portion 8 of the proximal head 4.

The proximal head 4 comprises a proximal conical portion 9 extending proximally along the shaft axis 6. The proximal conical portion 9 has a maximum transversal dimension defined by the maximum transversal dimension Dh of the proximal head 4 and a minimum transversal dimension Dmin defining a proximal surface 10 of the proximal head 4, with respect to the shaft axis 6.

The proximal conical portion 9 comprises at the proximal surface 10 a tool receiving seat 12 suitable for receiving an insertion tool (not shown).

The proximal head 4 comprises a central cylindrical portion 13 extending proximally from the distal spherical portion 8 along the shaft axis 6 at the maximum transversal dimension Dh of the proximal head 4.

The proximal conical portion 9 extends proximally from the central cylindrical portion 13 along the shaft axis 6.

Preferably the elongated member 2 is a cannulated screw comprising a axial channel 20 extending along the shaft axis 6 through the proximal head 4 and the elongated shaft 5 and opening out into the exterior through a fenestrations 21 arranged at the distal end 7 of the elongated shaft 5.

Through the axial channel 20 can pass a guide wire in order to put the elongated member 2 in position. Moreover the axial channel 20 can be used to insert bone cement through fenestrations 21 and a distal aperture 22 to improve fixation. A fluid preparation of bony cement is injected by a cannula that fits into the axial channel 20, from here the cement can overflow through the lateral fenestrations 21 and when it dries it acts as additional fixation between the screw and bone.

When bone cement is not used, fenestrations 21 and the distal aperture 22 are useful for the bone growing. The bone tissue is expected to grow around the implant as a consequence of the surgical injury. The bony tissue can grow inside fenestrations and through, to build an additional anchoring of the screw to the bone In particular the elongated shaft 5 has a smooth portion 5a disposed in a proximal portion of the elongated shaft 5, starting from the head 4, and a threaded portion 5b which has preferably a dual lead thread. In this case the pitch can be greater than 4 mm.

The washer 3 is a single part, in the shape of a disc, of various sizes (external diameters). The washer 3 has a central cavity 14 configured to seat the proximal head 4 and comprising a central spherical portion 15 having the same diameter D of the distal spherical portion 8 of the proximal head 4.

The central spherical portion 15 extends along a washer axis 6' between a distal rim 16 and a proximal rim 17.

The distal rim 16 has a distal transversal dimension Dd larger than a maximum transversal dimension d of the elongated shaft 5 and smaller than the maximum transversal dimension Dh of the proximal head 4, with respect to the washer axis 6' and the shaft axis 6.

The proximal rim 17 is designed to have an interference with the central cylindrical portion 13 of the proximal head 4. In particular the proximal rim 17 has a proximal transversal dimension Dw larger than the maximum transversal dimension d of the elongated shaft 5 and slightly smaller than the maximum transversal dimension Dh of the proximal head 4, with respect to the washer axis 6' and the shaft axis 6.

The proximal transversal dimension Dw of the proximal rim 17 is larger than the distal transversal dimension Dd of the distal rim 16. The proximal rim 17 is configured to be elastically deformable by pressing the proximal head 4 through the proximal rim 17 along the shaft axis 6 and washer axis 6'.

With reference to the above mentioned definition of the words "distal" and "proximal" the distal rim 16 is disposed at a side of the washer 3 facing the elongated shaft 5 when assembled with the washer 3.

The central cavity 14 of the washer 3 comprises a conical diverging portion 18 outwardly extending from said distal rim 16 along the washer axis 6' towards the elongated shaft 5, when assembled with the washer 3.

The central cavity 14 of the washer 3 comprises a cylindrical portion 19 outwardly extending from the proximal rim 17 along the washer axis 3.

FIG. 4 shows a bone fixation kit comprising a bone fixation device 1 as disclosed above and an assembling device 22 configured to overcome the interference between the proximal head 4 and the proximal rim 17 and to push the proximal head 4 into the central cavity 14 of the washer 3. The assembling device 22 comprises a seat 23 suitable for receiving the washer 3. In FIG. 4 the assembling device 22 is a plier allowing to overcome the interference and to push the head into the spherical seat of the washer. The plier accommodates the washer 3 in one extremity 24a while pressing the proximal head 4 with the opposite extremity 24b.

When assembled, thanks to the spherical coupling of the relevant surfaces the proximal head 4 and the washer 3 can freely rotate and tilt and, due to the interference, the parts cannot be disassembled unless an appropriate force is intentionally applied.

With the device and kit according to the invention, the washer 3 can be mounted on the elongated member by the distal end of the latter, and slid along the elongated shaft until the proximal rim 17 touches the distal spherical portion 8 of the proximal head 4. At this point, the proximal head 4 can be seated into the washer 3 by using the assembling device 22.

Thanks to the above mentioned features it is possible to intraoperative chose the combination between the elongated member 2 and the washer 3 and assemble the bone fixation device 1 during the surgery.

In order to be able to intraoperative assemble the washer together with the head the tolerance between the two components are very strict. In particular interference between washer and head is 0.005-0.08 mm or 0.005-0.2 mm.

It is further possible to choose between washers suitable for different maximum transversal dimension Dh of the proximal head 4. The washers will be designed in different sizes, with a diameters larger than "Dh" by 2 to 15 mm or 2 to 25 mm. For example if the screw has a maximum transversal dimension Dh of 10 mm, the relevant washers can be designed in a diameter range of 12 to 25 mm, or between 12 and 35 mm.

Figure 5:
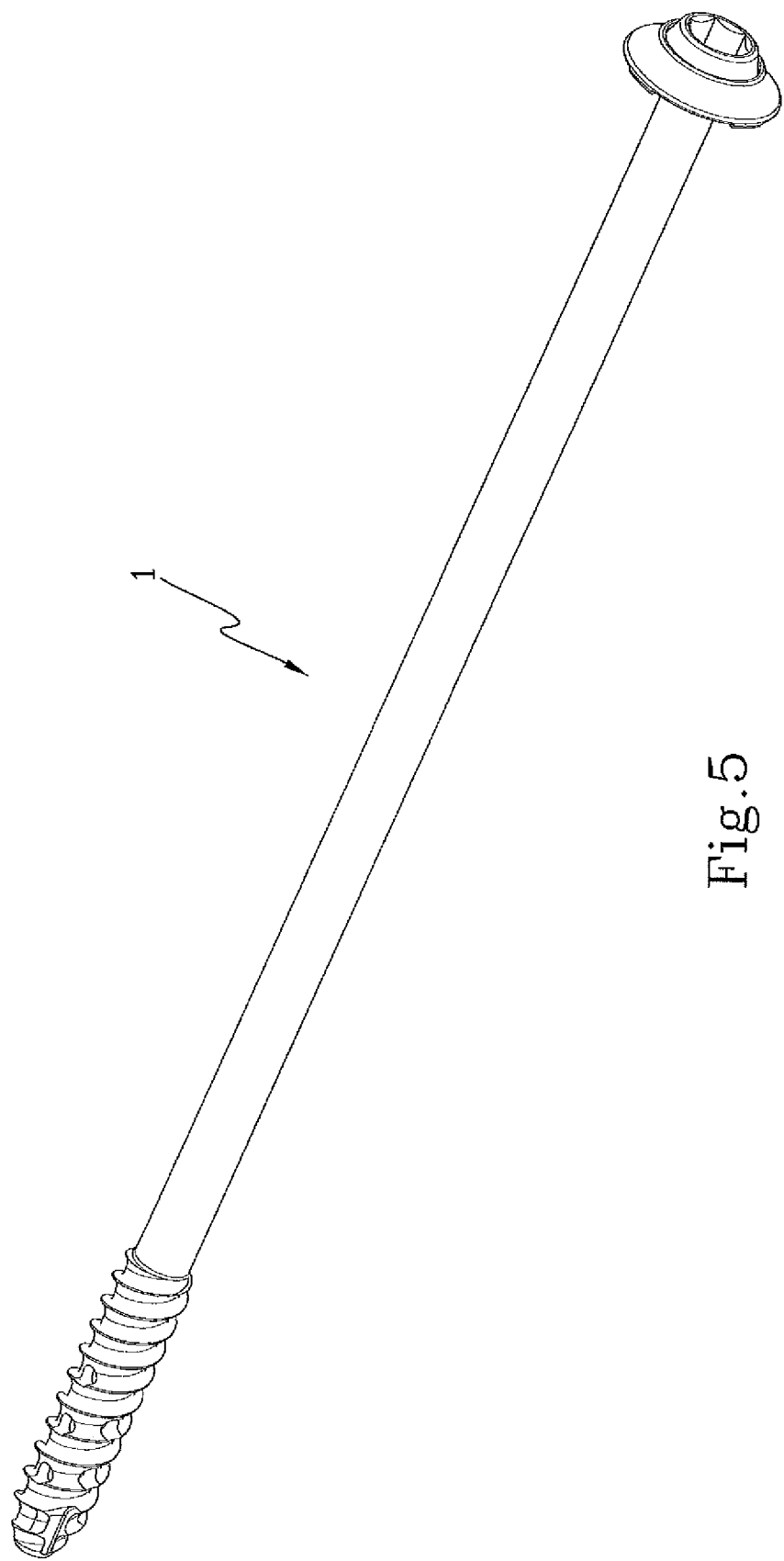
FIG. 5 shows a perspective view of an embodiment of a bone fixation device according to the present invention.
Figure 6:
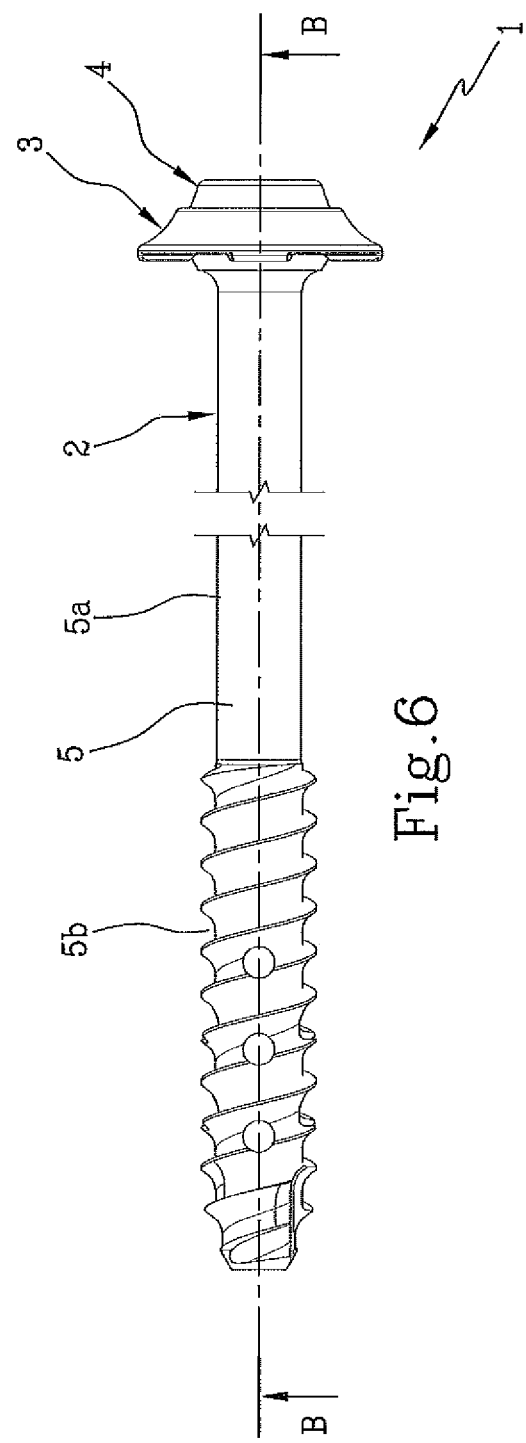
FIG. 6 shows a side view of the bone fixation device of FIG. 5.
Figure 7:
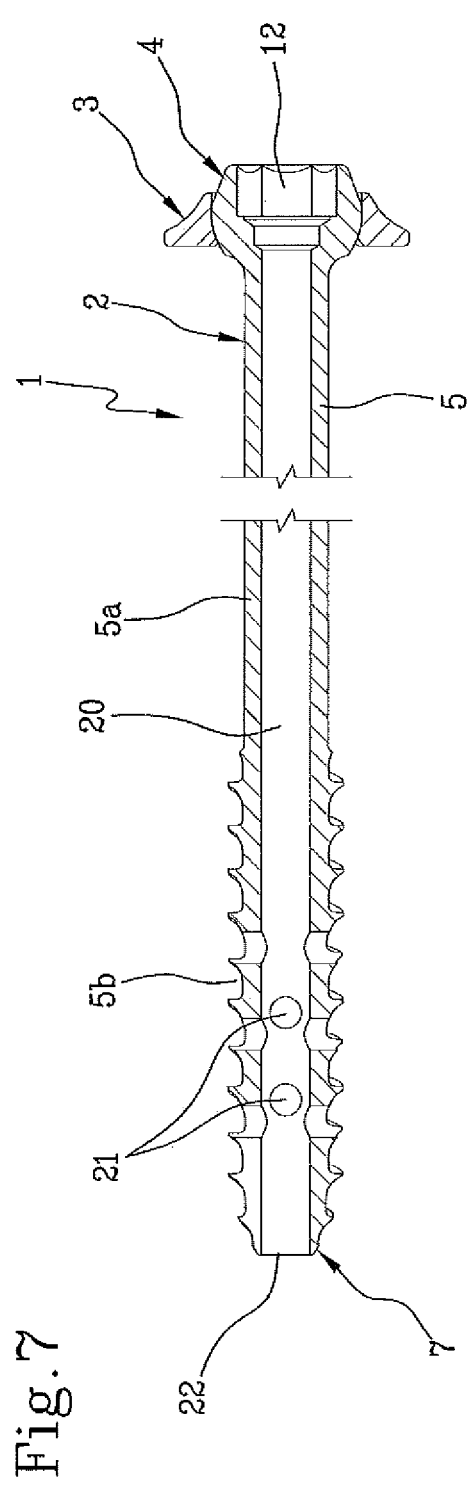
FIG. 7 shows a cross section view B-B of the bone fixation device of FIG. 6.

FIGS. 5-7 are related to a bone fixation device 1 for trauma applications, like the preceding embodiment, in which the elongated member 2 is long about 180 mm. Reference numbers are identical with the reference numbers used in the preceding embodiment. Characterizing features of the head 4 and washer 3 are the same.

FIGS. 8-10 are related to a bone fixation device 1 for SI-Joint Arthrodesis. The elongated member 2 is shorter with respect to the preceding embodiments and does not have a smooth portion or has a very short smooth portion. The threaded portion has a dual lead thread. Fenestrations 21 are elongated along the axis 6. Reference numbers are identical with the reference numbers used in the preceding embodiment. Characterizing features of the head 4 and washer 3 are the same.

The embodiments disclosed above can be provided with a screw having a single lead thread.

The invention claimed is:

1. A bone fixation device comprising an elongated member and a washer suitable for being assembled in a manner to prevent relative longitudinal displacement at the same time allowing axial rotation of the washer with respect of the elongated member, wherein the elongated member comprises a proximal head and an elongated shaft extending from the proximal head along a shaft axis towards a distal end of the elongated member, the proximal head comprising at least a distal spherical portion having a diameter and defining a maximum transversal dimension of the proximal head with respect to the shaft axis, wherein the washer has a central cavity configured to seat the proximal head and comprising a central spherical portion having the same diameter of the distal spherical portion of the proximal head, the central spherical portion extending along a washer axis between a distal rim and a proximal rim, the distal rim having a distal transversal dimension larger than a maximum transversal dimension of the elongated shaft and smaller than the maximum transversal dimension of the proximal head, with respect to the washer axis and the shaft axis, the proximal rim having a proximal transversal dimension larger than the maximum transversal dimension of the elongated shaft and slightly smaller than the maximum transversal dimension of the proximal head, with respect to the washer axis and the shaft axis, wherein the proximal transversal dimension of the proximal rim is larger than the distal transversal dimension of the distal rim and wherein the proximal rim is configured to be elastically deformable by pressing the proximal head through the proximal rim along the shaft axis and washer axis;

wherein the maximum transversal dimension of the proximal head is smaller than the diameter of the spherical portion of the proximal head.

2. The bone fixation device according to claim 1, wherein the distal rim is disposed at a side of the washer facing the elongated shaft when assembled with the washer.

3. The bone fixation device according to claim 1, wherein the central cavity of the washer comprises a conical diverging portion outwardly extending from said distal rim along the washer axis towards said elongated shaft, when assembled with the washer.

4. The bone fixation device according to claim 1, wherein the central cavity of the washer comprises a cylindrical portion outwardly extending from said proximal rim along the washer axis.

5. The bone fixation device according to claim 1, wherein the proximal head comprises a proximal conical portion extending proximally along the shaft axis, the proximal conical portion having a maximum transversal dimension defined by the maximum transversal dimension of the proximal head and a minimum transversal dimension defining a proximal surface of the proximal head, with respect to the shaft axis.

6. The bone fixation device according to claim 5, wherein the proximal conical portion comprises at the proximal surface a tool receiving seat suitable for receiving an insertion tool.

7. The bone fixation device according to claim 5, wherein the proximal head comprises a central cylindrical portion extending proximally from the distal spherical portion along the shaft axis at the maximum transversal dimension of the proximal head and wherein proximal conical portion extends proximally from the central cylindrical portion along the shaft axis.

8. The bone fixation device according to claim 1, wherein the proximal head comprises a central cylindrical portion extending proximally from the distal spherical portion along the shaft axis at the maximum transversal dimension of the proximal head.

9. The bone fixation device according to claim 1, wherein the elongated member is a cannulated screw having a length up to 180 mm for trauma applications or being shorter for SI-Joint arthrodesis and comprising a single or dual lead thread.

10. The bone fixation device according to claim 1, wherein interference between washer and proximal head is 0.005-0.2 mm.

11. A bone fixation kit comprising a bone fixation device (1) according to claim 1 and an assembling device (22) configured to overcome the interference between the proximal head (4) and the proximal rim (17) and to push the proximal head (4) into the central cavity (14) of the washer (30).

12. A]bone fixation kit according to claim 11, wherein the assembling device (22) comprises a seat (23) suitable for receiving the washer (3).

13. The bone fixation device according to claim 1, wherein the interference between washer and proximal head is 0.005-0.08 mm.

* * * * *